United States Patent [19]
Gallagher, Jr. et al.

[11] 3,939,172
[45] Feb. 17, 1976

[54] 4-AMINOTHIAZOLE

[75] Inventors: Gregory Gallagher, Jr., Collegeville; William D. Kingsbury, West Chester, both of Pa.

[73] Assignee: SmithKline Corporation, Philadelphia, Pa.

[22] Filed: Nov. 7, 1974

[21] Appl. No.: 521,707

[52] U.S. Cl....... 260/306.8 R; 260/239.95; 424/229
[51] Int. Cl.².............. C07D 277/40; C07D 277/46
[58] Field of Search............................. 260/306.8 R

[56] References Cited
OTHER PUBLICATIONS

Elderfield (ed.), *Heterocyclic Compounds*, Vol. 5, N.Y., John Wiley & Sons, 1957, p. 587.

*Primary Examiner*—Richard J. Gallagher
*Attorney, Agent, or Firm*—William H. Edgerton

[57] ABSTRACT

4-Aminothiazole is prepared in stable useful form by alkaline hydrolysis of 4-trifluoroacetamidothiazole. Also prepared are 4-sulfathiazole and 2-(4-thaizolyl)-indazole.

10 Claims, No Drawings

4-AMINOTHIAZOLE

BACKGROUND OF THE INVENTION

4-Aminothiazole is an intermediate long sought in medicinal chemistry but hitherto unavailable because of the lack of operant procedures and because of the lability of 4-aminothiazole itself as well as possible intermediates for preparing it. 2-Aminothiazole is a well known and widely used intermediate. It is relatively stable as well as easy to use and prepare. The 2-isomer of the art is stable because of resonant forms possible with the 2-amino form. At the 4-position these resonant forms do not stabilize the ring making the 4-aminothiazole nucleus more susceptible to hydrolysis with the formation of unknown water soluble products.

4-Aminothiazole was mentioned in a physiochemical study of the thiazole ring but this publication refers to no method of preparation (Bull. Soc. Chim. Fr. 1967 3283–3293 C.A. 68 44384 m). In fact, examination of this paper reveals that the only data published on the compound are those theoretically observed but not actually measured using the compound itself. Therefore there is a strong inference that the compound was not in hand for this study.

In 1973, 4-aminothiazole was erroneously indexed by Chemical Abstracts (79, 32088g). The parent reference does not mention the compound. Various derivatives of 4-aminothiazole having stabilizing nuclear substitution have been reported especially the 2-bromo derivatives (U.S. Pat. No. 3,244,723) but to the best of our knowledge, 4-aminothiazole itself has not been reported to be isolated in a form useful for synthetic purposes.

THIS INVENTION

The invention comprises a series of related components, first the essential N-trifluoroacetyl derivative of 4-aminothiazole, the unique method of hydrolyzing the N-trifuoroacetyl derivative, 4-aminothiazole itself, and 4-sulfanilamidothiazole or 2-(4-thiazolyl)indazole prepared therefrom.

DETAILS OF THE INVENTION

4-Trifluoroacetamidothiazole is prepared in high yield by catalytic hydrogenation of 2-bromo-4-trifluoroacetamidothiazole using a noble metal calalyst such as palladium, platinum, raney nickel, etc. under standard dehalogenation conditions, that is a low pressure hydrogen atmosphere at about room temperature or slightly higher in a Parr shaker.

The protective trifluoroacetyl group of the unique starting material of this invention is then removed by alkaline hydrolysis. The hydrolysis is most advantageously carried out in aqueous media, in solution or suspension, using a base which is strong enough to generate an amido anion in the acetamido moiety, most conveniently at about pH 11 or greater. Such bases are most usually ammonium or alkali metal hydroxides preferably calcium, sodium or potassium hydroxide. The amount of base has been defined above but should be present in the amount of at least one mole equivalent and preferably in large excess to maintain the necessary basic pH of the reaction medium.

The solvent system is ordinarily water but inert organic solvents miscible with water also may be used such as methanol, ethanol, acetone, etc. Aqueous media as known generally to the art are therefore used in the reaction. The reaction temperature is critical with the most advantageous temperature range from the viewpoint of yield and time of reaction being from about 30°–35°C. Below 30°C., for example at room temperature, the reaction takes place more slowly. Above 40°C. side reactions occur which make isolation of the desired product most difficult. The time of reaction may vary up to about 18 hours but periods of about 4–8 hours are preferred.

The reaction mixture is worked up by standard methods such as neutralizing the mixture, removal of the water and distillation of the residue to give a distillate at about 40°C./0.1 mm. Hg. which crystallizes to the desired 4-aminothiazole as white needle like crystals melting at 26°–28°C. in a sealed tube but at 91°–94°C. after initial melting. This indicates that polymorphic forms of the compound are possible. The material is stable when refrigerated under an inert atmosphere but it decomposes rapidly in the open atmosphere and is highly hygroscopic.

The trifluoroacetyl group is considered the key to the successful production of this long missing compound. Attempts to use acetyl or nitrobenzoyl protective groups both of which are specifically mentioned in U.S. Pat. No. 3,244,723 do not give practically isolable quantities of the desired product. This is unexpected since the nitrobenzoyl moiety is known to the art for its stabilizing effect on unstable amines.

UTILITY OF 4-Aminothiazole

As mentioned above the compound which is the object of this invention is a valuable intermediate for preparing any number of end products having various medicinal activities usually chemotherapeutic such as antibacterials or antiparasitics. For example, Burger's "Medicinal Chemistry", 3rd Ed. 1970, page 722, expressly mentions 2 and 5-sulfathiazoles but conspicuously omits reference to the only remaining C-isomer namely the 4-sulfathiazole which can only be prepared using 4-aminothiazole.

In fact, we have now made 4-sulfanilamidothiazole using 4-aminothiazole as an intermediate and found it a very active antibacterial agent against sulfasensitive Bordetella bronchiseptica.

| Concentration ($\mu$g/ml.) | Strain B Zone size (mm.) | Strain VMRT Zone size (mm.) |
|---|---|---|
| 1000 | 35 | 30 |
| 500 | 31 | 27 |
| 250 | 29 | 25 |
| 125 | 26 | 22 |
| 62.5 | 24 | 20 |
| 31.3 | 20 | 16 |
| 15.6 | 16 | 12 |
| 7.8 | 12 | none |
| 3.9 | none | none |

Alternatively 4-thiazolylindazoles may be prepared by reacting 4-aminothiazole with an appropriate o-nitrobenzaldehyde to give the Schiff base which is then cyclized to the corresponding 2-(4-thiazolyl)indazole. The indazoles are anthelmintic agents especially active against gastrointestinal helminths such as the nematodes. The spectrum of activity resembles that of thiabendazole. The corresponding 1-(2-thiazolyl)indazoles have been patented (U.S. Pat. No. 3,759,903). Other nuclear substituents or salts as well as general utility of the claimed 2-(4-thiazolyl)indazoles are similar.

EXAMPLE 1

2-Bromo-4-Aminothiazole, hydrobromide

A solution of 70 g. (0.71 mole) of cyanomethylthiocyanate (U.S. Pat. No. 3,244,723) in 2 l of dry ethyl ether is treated with dry HBr gas for 75 minutes at 15°–20°C. Stirring at room temperature is continued for one-half hour. The white precipitate is filtered, washed quickly with ethyl ether followed by n-pentane and dried in vacuo to yield 176.9 g. (96%) of white powder.

2-Bromo-4-trifluoroacetamidothiazole, trifluoroacetic acid salt

To 270 g. (1.3 moles) of trifluoroacetic anhydride is added 100 g. (0.385 mole) of the hydrobromide in four portions as each portion dissolves. The clear pale yellow solution is allowed to cool over 1 hour. The excess anhydride is removed by atmospheric distillation and the residual trifluoroacetic acid is stripped off in vacuo at 40°C. The light tan solid is dried one hour under pump vacuum to give 125.2 g.

2-Bromo-4-trifluoroacetamidothiazole

A solution of 125 g. of the above compound in 500 ml. of ethanol is passed through a column of 400 cc of the sodium salt of an acid ion-exchange resin (Amberlite IRC-50). The free base is eluted with two volumes of ethanol and the total effluent is concentrated in vacuo. The residue is extracted with 600 ml. of hot hexane. The hot extract is treated with 2 g. of activated charcoal and allowed to cool. The white crystals are filtered and air-dried to give 65 g. The mother liquor is evaporated to dryness and the residue crystallized from hexane to give an additional 8.7 g. of white needles m.p. 67°–9°C.

4-Trifluoroacetamidothiazole

A mixture of 50 g. (0.182 mole) of 2-bromo-4-trifluoroacetamidothiazole 36.5 g. (0.268 mole) of sodium acetate, trihydrate and 16.6 g. of 10% palladium on carbon in 1.5 l. of absolute ethanol is hydrogenated at one atmosphere over 18 hours at room temperature. The catalyst is filtered off and washed well with ethanol. The filtrate is evaporated to dryness and the residue extracted several times with warm methylene chloride. The combined extracts are evaporated to dryness and the residue crystallized from carbon tetrachloride (activated carbon treatment) to give 25 g (70%) of heavy white crystals m.p. 138°–9°C. Recrystallization of the second crop obtained from the mother liquor raises the yield to 28.5 g. (80%). The product can also be satisfactorily recrystallized from ethanol/water mixtures.

Acid addition salts of the base are prepared as disclosed for 4-aminothiazole hereafter but if only one basic center is present of course mono salts are formed. The trifluoroacetic acid salt is of particular interest.

4-Aminothiazole

To a suspension of 5.90 g. (0.03 mole) of finely ground 4-trifluoromethylacetamidothiazole in 45 ml. of water is added 50% aqueous sodium hydroxide dropwise until a complete solution is obtained. Efficient stirring will cause this to occur after about 3 ml. of base has been added. The solution is then stirred at 30°–35°C. for 6 hours under an inert atmosphere. The reaction solution is cooled in an ice-bath and the pH adjusted to about 8.5 with glacial acetic acid. The water is then removed in vacuo at <40°C. and the residue immediately subjected to vacuum-distillation using a short path distillation apparatus with an ice-cooled receiver. When the heating bath temperature reaches about 160°C. the distillation is terminated and the system vented with dry nitrogen gas. The distillate boils at about 40°C./0.1 mm. Hg. and quickly crystallizes in the cold receiver to give 1.60 g. (54%) of hygroscopic white crystals which are kept cold under a nitrogen atmosphere. m.p. (sealed tube) 26°–28°C. (remelt at 91°–94°C.).

EXAMPLE 2

4-($N^4$-acetylsulfanilamido)thiazole

A cold solution of 1.60 g. (0.016 mole) of 4-aminothiazole in 20 ml. of dry pyridine is treated with 4.0 g. (0.017 mole) of acetylsulfanilyl chloride in small portions over 15 minutes. The reaction is allowed to warm slowly to room temperature and stirring continued for about 2 days. The red solution is diluted slowly with 120 ml. of water and then cooled in an ice-bath for 1½ hours. The crystalline precipitate is collected and washed with a small amount of cold dilute hydrochloric acid followed by several portions of water. The yield of the air-dried cream-colored product is 4.10 g. (86%) m.p. 231°–2°C.

4-Sulfanilamidothiazole (4-sulfathiazole)

A solution of 4.0 g. (0.0135 mole) of the N-acetyl compound in 120 ml. of ethanol and 12 ml. of concentrated hydrochloric acid is heated for 2½ hours on a steam bath. The reaction is cooled with an ice-bath and neutralized with about 120 ml. of 5% sodium hydroxide. The precipitate is collected, washed with water and air-dried to give 2.70 g. Recrystallization from 100 ml. of ethanol and 40 ml. of water gives 2.00 g. (58%) of white needles m.p. 221°–2°C. Note: The hydrolysis may also be effected in alkaline media.

EXAMPLE 3

2-(4-thiazolyl)-indazole

A solution of 7.70 g. of o-nitrobenzaldehyde in 150 ml. of absolute ethanol is reacted with .051 moles of 4-aminothiazole in 90 ml. of water at room temperature at pH 4.5 for one-half hour. The Schiff base is separated and reacted (7 g.) in 11.4 g. of triethyl phosphite by heating slowly under nitrogen then at reflux for 5 hours. Distilling of excess phosphite and phosphate under reduced pressure gives a residue which is taken up in 35 ml. of chloroform. Chromatography in 4:1 ether-chloroform over silica gel gives the product as white crystals, m.p. 146°–147°C.

Also useful are the acid addition salts of 4-aminothiazole (or its predecessor 4-trifluoroacetamidothiazole) with various acids especially nontoxic, pharmaceutically acceptable acids known to the art. Since the compounds are used solely as intermediates, the acids do not necessarily have to be nontoxic. One skilled in the art will recognize that there are two potential basic centers in 4-aminothiazole. The acid addition salts are easily prepared by standard reactions for example by dissolving the base in dry ethyl ether and adding the appropriate acid in at least stoichiometric quantities. The hydrochloride salt is prepared by dissolving 500 mg. of 4-aminothiazole in dry ethyl ether, then passing dry hydrogen chloride gas into the mixture to separate the salt which is hygroscopic but which can be purified by recrystallization from acetonitrile.

Salts can be optimally prepared with other acids such as inorganic or organic acids as hydrogen bromide, sulfuric acid, acetic acid, malic acid, maleic acid, methyl sulfonic acid, toluene sulfonic acid, phosphoric acid, sulfamic acid, oxalic acid, etc.

In general 4-aminothiazole is a stronger base than is its 2-isomer which is widely known in the art so that any salt known for the 2-isomer can be prepared from the 4-isomer of this invention. The nontoxic acid addition salts of the two classes of end products described herein are also prepared by methods well known to the art and are similar to those described except of course for other simple derivatives of the 4-sulfathiazole which are common to the well known sulfa prior art.

What is claimed is:

1. 4-Aminothiazole and its acid addition salts.
2. The compound of claim 1 being the base of the structure:

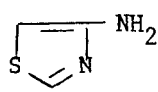

3. The compound of claim 1 being the hydrochloride salt of 4-aminothiazole.
4. 4-Trifluoroacetamidothiazole and its acid addition salts.
5. The compound of claim 4 being the base of the structure:

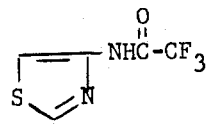

6. The compound of claim 4 being the trifluoroacetic acid salt of 4-trifluoroacetamidothiazole.
7. The method of preparing 4-aminothiazole comprising reacting 4-trifluoroacetamidothiazole with an ammonium or alkali metal hydroxide in an aqueous medium at from about room temperature up to about 40°C. until the hydrolysis reaction is substantially complete.
8. The method of claim 7 in which the hydroxide is sodium or potassium hydroxide and the temperature range is from about 30°–35°C.
9. The method of claim 8 in which the reaction time is from about 4–8 hours.
10. The method of preparing 4-aminothiazole comprising reacting 2-bromo-4-trifluoroacetamidothiazole under low pressure catalytic hydrogenation conditions in the presence of a noble metal catalyst to give 4-trifluoroacetamidothiazole then reacting said 4-trifluoroacetamidothiazole with sodium or potassium hydroxide in an aqueous medium at from about 30°–35°C. for about 4–8 hours.

* * * * *